(12) United States Patent
Kuwahara et al.

(10) Patent No.: US 8,192,814 B2
(45) Date of Patent: Jun. 5, 2012

(54) TUBE AND MEDICAL DEVICE COMPRISING THE SAME

(75) Inventors: Shigenao Kuwahara, Ibaraki (JP); Hidetaka Oonuma, Ibaraki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 180 days.

(21) Appl. No.: 12/676,753

(22) PCT Filed: Sep. 4, 2008

(86) PCT No.: PCT/JP2008/065994
§ 371 (c)(1),
(2), (4) Date: Mar. 5, 2010

(87) PCT Pub. No.: WO2009/031625
PCT Pub. Date: Mar. 12, 2009

(65) Prior Publication Data
US 2010/0239802 A1  Sep. 23, 2010

(30) Foreign Application Priority Data

Sep. 7, 2007 (JP) .................................. 2007-232687
Jul. 23, 2008 (JP) .................................. 2008-189274

(51) Int. Cl.
*B29D 22/00* (2006.01)

(52) U.S. Cl. ................... 428/35.7; 428/36.9; 428/36.91; 604/264; 138/118

(58) Field of Classification Search ................ 428/35.7, 428/36.9, 36.91; 525/89; 604/264, 96
See application file for complete search history.

(56) References Cited

U.S. PATENT DOCUMENTS

| | | | | |
|---|---|---|---|---|
| 5,264,488 A | * | 11/1993 | Takeuchi et al. ................ | 525/89 |
| 6,310,138 B1 | * | 10/2001 | Yonezawa et al. .............. | 525/88 |
| 7,147,905 B2 | * | 12/2006 | Fukuda et al. ............. | 428/36.91 |
| 7,247,674 B2 | * | 7/2007 | Kitano et al. .................... | 525/93 |
| 7,267,855 B2 | * | 9/2007 | Handlin et al. ............... | 428/34.1 |
| 7,615,272 B2 | * | 11/2009 | Nakaya et al. ............... | 428/35.7 |
| 7,618,696 B2 | * | 11/2009 | Wang et al. ................ | 428/36.92 |
| 7,906,584 B2 | * | 3/2011 | Suzuki et al. ................... | 525/93 |
| 2005/0239962 A1 | * | 10/2005 | Yoo et al. ........................ | 525/71 |
| 2008/0161485 A1 | * | 7/2008 | Suzuki et al. ................... | 524/575 |
| 2010/0087559 A1 | * | 4/2010 | Kusanose et al. ............. | 521/148 |
| 2010/0239802 A1 | * | 9/2010 | Kuwahara et al. ............ | 428/36.9 |

FOREIGN PATENT DOCUMENTS

| | | |
|---|---|---|
| JP | 2 300250 | 12/1990 |
| JP | 4 159344 | 6/1992 |
| JP | 10 67894 | 3/1998 |
| JP | 2001 1432 | 1/2001 |
| JP | 2002 248671 | 9/2002 |
| JP | 2003 287163 | 10/2003 |
| JP | 2004 124070 | 4/2004 |
| JP | 2004 194803 | 7/2004 |
| JP | 2004 346109 | 12/2004 |
| WO | 2006 134974 | 12/2006 |

* cited by examiner

*Primary Examiner* — N. Edwards
(74) *Attorney, Agent, or Firm* — Oblon, Spivak, McClelland, Maier & Neustadt, L.L.P.

(57) ABSTRACT

The present invention relates to a tube in the form of a molded article of a resin composition including a hydrogenated block copolymer (a) which includes a polymer block constituted mainly from an aromatic vinyl compound unit and a polymer block constituted mainly from a specific conjugated diene compound unit and has a glass transition temperature of from −45 to 30° C., a hydrogenated block copolymer (b) which includes a polymer block constituted mainly from an aromatic vinyl compound unit and a polymer block constituted mainly from a specific conjugated diene compound unit and has a glass transition temperature of less than −45° C., and a polyolefin-based resin (c), at a specific proportion, said tube being excellent in transparency, flexibility, anti-kinking property, anti-sticking property, clamp resistance, solvent adhesion property, low-temperature impact resistance and heat resistance, as well as a medical device using the tube.

20 Claims, No Drawings

TUBE AND MEDICAL DEVICE COMPRISING THE SAME

TECHNICAL FIELD

The present invention relates to tubes which are excellent in transparency, flexibility, anti-kinking properties, anti-sticking properties, etc., and medical devices using the same.

BACKGROUND ART

Hitherto, there have been proposed various hydrogenated block copolymers of A-(B-A)$_n$ type or (A-B)$_n$ type (wherein n is an integer of 1 or more) which are composed of a polymer block (A) constituted mainly from an aromatic vinyl compound unit and a polymer block (B) constituted mainly from a conjugated diene unit and in which a carbon-to-carbon double bond derived from the conjugated diene unit is hydrogenated. The hydrogenated block copolymers have been used as an alternate material of vulcanized rubbers or soft vinyl chloride-based resins for production of various molded articles.

Also, it is known that polyolefin-based resins which are excellent in oil resistance, heat resistance, chemical resistance and processability but insufficient in flexibility, transparency and impact resistance are compounded with the above hydrogenated block copolymers to prepare polyolefin compositions which are improved in flexibility, transparency and impact resistance and free from generation of toxic gases when incinerated upon disposal thereof. The polyolefin compositions have been extensively used as an alternate material of soft vinyl chloride-based resins in various applications such as food transportation, parts of household appliances and medical devices (refer to Patent Documents 1 and 2).

However, tubes obtained by molding the polyolefin compositions prepared by compounding the polyolefin-based resins with the above hydrogenated block copolymers tend to frequently suffer from occurrence of undesirable phenomena such as collapse or break of the tubes because they fail to exhibit a sufficient resistance to deformation caused when bending the tubes into a ring shape or an arcuate shape. To solve such a problem, Patent Documents 3 and 4 disclose the methods for improving an endotracheal tube and a tube, respectively. However, the method described in Patent Document 3 has failed to sufficiently improve deformation, collapse, etc., of the tube, whereas the method described in Patent Document 4 tends to cause stickiness between the tubes owing to the use of a softening agent for rubbers therein, which results in poor handling property of the tubes. In particular, in medical applications, there tends to occur the problem that when clamping the tube with forceps, inner surface portions of the tube are stuck together, resulting in poor restoration of the tube into its original shape even after removing the forceps therefrom, or the problem that the tubes are stuck with each other after subjected to sterilization in an autoclave.

To solve the problem of stickiness between the tubes, Patent Document 5 discloses a soft polymer composition including a block copolymer composed of polystyrene and an ethylene-propylene copolymer, a block copolymer composed of polystyrene and an ethylene-butylene copolymer, and a polyolefin. However, the polymer composition still has the problem that its transparency is insufficient owing to poor compatibility between the block copolymers.

In addition, when used in medical applications, it is required that the tubes are coupled to various connectors. However, since the polyolefin-based resins are not dissolved in a solvent, the polymer composition containing a large amount of the polyolefin-based resins tends to show a poor adhesion strength upon bonding with a solvent. Patent Document 6 discloses a multi-layered tube comprising (a) a polypropylene-based resin and (b) a resin composition containing a polymer block constituted from an aromatic vinyl compound unit for the purpose of improving a solvent-bonding property thereof. However, owing to the multi-layered structure of the tube, it is difficult to form the respective layers having a uniform thickness.

Further, Patent Document 7 discloses a medical device such as tubes which comprises (a) a hydrogenated block copolymer obtained by hydrogenating a block copolymer composed of a polymer block constituted mainly from an aromatic vinyl compound unit and a polymer block constituted mainly from a conjugated diene compound unit, and (b) a high-crystalline propylene-based resin.

In the applications such as medical devices and food transportation, the tubes are frequently used under a low-temperature condition for maintaining a good quality of contents therein and, therefore, required to have an excellent performance capable of withstanding an impact force upon falling or dropping even under a low-temperature condition by which the tubes can be prevented from suffering from breakage, etc.

Patent Document 1: JP 2-300250A
Patent Document 2: JP 10-67894A
Patent Document 3: JP 2002-248671A
Patent Document 4: JP 2003-287163A
Patent Document 5: JP 4-159344A
Patent Document 6: JP 2001-1432A
Patent Document 7: JP 2004-194803A

DISCLOSURE OF THE INVENTION

Thus, it is an object of the present invention to provide a tube that is excellent in transparency, flexibility, anti-kinking property, anti-sticking property, clamp resistance, solvent-bonding property, low-temperature impact resistance and heat resistance, as well as a medical device using the tube.

Meanwhile, the "anti-kinking property" as used herein means a property of a tube which is capable of withstanding abnormal deformation such as buckling which tends to occur when bending the tube into a ring shape or an arcuate shape. The "clamp resistance" as used herein means a property of a tube which is capable of restoring its original shape immediately after releasing a medical forceps from the tube clamped therewith out any stickiness between inner surfaces of the tube. The "solvent-bonding property" as used herein means a property of a tube which is capable of showing a sufficient adhesion strength when coupled with connectors through a solvent. The "low-temperature impact resistance" as used herein means a property of a tube which is capable of withstanding an impact force exerted thereto upon falling or dropping under a low-temperature condition and preventing the tube from suffering from breakage, etc. The "heat resistance" as used herein means a property of a tube which is free from stickiness between tubes after subjected to sterilization in autoclave.

As a result of extensive and intensive researches for solving the above conventional problems, the present inventors have found that these problems can be solved by a tube comprising a resin composition containing two kinds of specific hydrogenated copolymers and a specific polyolefin-based resin at a specific proportion. The present invention has been accomplished on the basis of the above finding.

Thus, the present invention provides the following aspects (1) to (8).

(1) A tube comprising a molded article of a resin composition comprising a hydrogenated block copolymer (a), a hydrogenated block copolymer (b) and a polyolefin-based resin (c), wherein the hydrogenated block copolymer (a) is formed by hydrogenating a block copolymer comprising at least a polymer block (A) constituted mainly from an aromatic vinyl compound unit and a polymer block (B) constituted mainly from a 1,3-butadiene unit or constituted mainly from an isoprene unit and a 1,3-butadiene unit; a content of the polymer block (A) is from 5 to 40% by mass on the basis of a total amount of the hydrogenated block copolymer (a); the polymer block (B) has a hydrogenation rate of 70% or more; and the hydrogenated block copolymer (a) has a glass transition temperature of from −45 to 30° C., wherein the hydrogenated block copolymer (b) is formed by hydrogenating a block copolymer comprising at least a polymer block (C) constituted mainly from an aromatic vinyl compound unit and a polymer block (D) constituted mainly from a 1,3-butadiene unit or constituted mainly from an isoprene unit and a 1,3-butadiene unit; a content of the polymer block (C) is from 10 to 40% by mass on the basis of a total amount of the hydrogenated block copolymer (b); the polymer block (D) has a hydrogenation rate of 80% or more; and the hydrogenated block copolymer (b) has a glass transition temperature of less than −45° C., and wherein a mass ratio of the hydrogenated block copolymer (a) to the hydrogenated block copolymer (b) [(a)/(b)] is from 50/50 to 95/5; and a mass ratio of the polyolefin-based resin (c) to a sum of the hydrogenated block copolymer (a), the hydrogenated block copolymer (b) and the polyolefin-based resin (c) [(c)/((a)+(b)+(c))] is from 10/100 to 60/100.

(2) The tube as defined in the above aspect (1), wherein the polymer block (B) of the hydrogenated block copolymer (a) is constituted mainly from an isoprene unit and a 1,3-butadiene unit.

(3) The tube as defined in the above aspect (2), wherein the polymer block (D) of the hydrogenated block copolymer (b) is constituted mainly from an isoprene unit and a 1,3-butadiene unit.

(4) The tube as defined in the above aspect (2) or (3), wherein the hydrogenated block copolymer (a) is in the form of a hydrogenated tri-block copolymer formed by hydrogenating a block copolymer having a A1-B-A2 type structure which comprises a polymer block (A1) and a polymer block (A2) each constituted mainly from an aromatic vinyl compound unit, and a polymer block (B) constituted mainly from an isoprene unit and a 1,3-butadiene unit, and a mass ratio of a weight-average molecular weight [Mw(A1)] of the polymer block (A1) to a weight-average molecular weight [Mw(A2)] of the polymer block (A2) [Mw(A1)/Mw(A2)] is from 0.10 to 1.00.

(5) The tube as defined in any one of the above aspects (1) to (4), wherein the hydrogenated block copolymer (b) is a mixture of a tri-block copolymer and a di-block copolymer.

(6) The tube as defined in any one of the above aspects (1) to (5), wherein the polyolefin-based resin (c) has a melt flow rate of from 0.2 to 50 g/10 min as measured at 230° C. under a load of 21.2 N.

(7) The tube as defined in any one of the above aspects (1) to (6), wherein the polyolefin-based resin (c) is a propylene homopolymer, a copolymer of propylene and ethylene or a mixture thereof, and has an ethylene content of from 0 to 30%.

(8) A medical device using the tube as defined in any one of the above aspects (1) to (7).

In accordance with the present invention, with the above construction, it is possible to provide a tube which is excellent in transparency, flexibility, anti-kinking property, anti-sticking property, clamp resistance, solvent-bonding property, low-temperature impact resistance and heat resistance. In particular, the tube of the present invention can be suitably used as a medical device.

BEST MODE FOR CARRYING OUT THE INVENTION

Hydrogenated Block Copolymers (a) and (b)

The hydrogenated block copolymer (a) used as a first component in the present invention is formed by hydrogenating a block copolymer containing at least a polymer block (A) constituted mainly from an aromatic vinyl compound unit and a polymer block (B) constituted mainly from a 1,3-butadiene unit or constituted mainly from an isoprene unit and a 1,3-butadiene unit, in which a content of the polymer block (A) is from 5 to 40% by mass on the basis of a total amount of the hydrogenated block copolymer (a); a hydrogenation rate of the polymer block (B) is 70% or more; and the hydrogenated block copolymer (a) has a glass transition temperature of from −45 to 30° C.

The hydrogenated block copolymer (b) used as a second component in the present invention is formed by hydrogenating a block copolymer containing at least a polymer block (C) constituted mainly from an aromatic vinyl compound unit and a polymer block (D) constituted mainly from a 1,3-butadiene unit or constituted mainly from an isoprene unit and a 1,3-butadiene unit, in which a content of the polymer block (C) is from 10 to 40% by mass on the basis of a total amount of the hydrogenated block copolymer (b); a hydrogenation rate of the polymer block (D) is 80% or more; and the hydrogenated block copolymer (b) has a glass transition temperature of less than −45° C.

The polymer block (A) of the hydrogenated block copolymer (a) and the polymer block (C) of the hydrogenated block copolymer (b) are respectively constituted mainly from an aromatic vinyl compound unit, and the content of the aromatic vinyl compound unit in the respective polymer blocks is preferably 80% by mass or more, and more preferably from 90 to 100%, and the respective polymer blocks are still more preferably constituted from the aromatic vinyl compound unit solely.

Examples of aromatic vinyl compounds from which the aromatic vinyl compound unit constituting each of the polymer block (A) of the hydrogenated block copolymer (a) and the polymer block (C) of the hydrogenated block copolymer (b) is derived include styrene, α-methyl styrene, 2-methyl styrene, 3-methyl styrene, 4-methyl styrene, 4-propyl styrene, 4-cyclohexyl styrene, 4-dodecyl styrene, 2-ethyl-4-benzyl styrene, 4-(phenylbutyl) styrene, 1-vinyl naphthalene and 2-vinyl naphthalene. Among these aromatic vinyl compounds, preferred are α-methyl styrene and 4-methyl styrene.

The polymer block (A) and the polymer block (C) may be respectively constituted from either one unit solely or two or more units derived from these aromatic vinyl compounds.

In addition, the polymer block (A) and the polymer block (C) may respectively contain the other polymerizable monomer unit unless inclusion of the unit adversely affects the object and effects of the present invention. For example, the polymer block (A) and the polymer block (C) may respectively contain a unit derived from a conjugated diene such as 1,3-butadiene, isoprene, 2,3-dimethyl-1,3-butadiene, 1,3-pentadiene and 1,3-hexadiene in a small amount and preferably in an amount of 20% by mass or less on the basis of the total amount of the respective polymer blocks.

Also, the polymer block (B) of the hydrogenated block copolymer (a) and the polymer block (D) of the hydrogenated block copolymer (b) are respectively constituted mainly from a 1,3-butadiene unit or constituted mainly from a mixed unit of an isoprene unit and a 1,3-butadiene unit. The content of the 1,3-butadiene unit or the mixed unit of the isoprene unit and the 1,3-butadiene unit in the respective polymer blocks is preferably 80% by mass or more, and more preferably from 90 to 100%, and the polymer blocks (B) and (D) are still more preferably constituted from the 1,3-butadiene unit solely (100% by mass) and the mixed unit of the isoprene unit and the 1,3-butadiene unit solely (100% by mass), respectively.

In addition, the polymer block (B) and the polymer block (D) may respectively contain the other polymerizable monomer unit, for example, a unit derived from the above aromatic vinyl compound, etc., in a small amount and preferably in an amount of 20% by mass or less on the basis of a total amount of the respective polymer blocks unless inclusion of the unit adversely affects the object and effects of the present invention.

The polymer block (B) of the hydrogenated block copolymer (a) and the polymer block (D) of the hydrogenated block copolymer (b) are respectively in the form of a polymer block constituted mainly from a 1,3-butadiene unit or constituted mainly from a mixed unit of an isoprene unit and a 1,3-butadiene unit as described above. The polymer block (B) is preferably constituted mainly from the mixed unit of an isoprene unit and a 1,3-butadiene unit, because the tube obtained from the resulting resin composition is suitably improved in transparency, anti-sticking property, etc. Further, both the polymer block (B) and the polymer block (D) are more preferably constituted from the mixed unit of an isoprene unit and a 1,3-butadiene unit, because the tube obtained from the resulting resin composition is suitably improved in transparency, anti-kinking property, anti-sticking property, etc.

The mixing ratio between 1,3-butadiene and isoprene from which the above mixed unit is derived is not particularly limited. From the viewpoint of improving properties of the obtained tube, etc., the mixing ratio of 1,3-butadiene to isoprene (1,3-butadiene/isoprene) (in terms of a molar ratio) is preferably from 10/90 to 90/10, more preferably from 30/70 to 70/30 and still more preferably from 40/60 to 60/40. The configuration of a polymer obtained from 1,3-butadiene and isoprene is not particularly limited, and the polymer may be in the form of either a block copolymer or a random copolymer.

It is important that the content of the polymer block (A) in the hydrogenated block copolymer (a) lies within the range of from 5 to 40% by mass on the basis of a total amount of the hydrogenated block copolymer (a). The content of the polymer block (A) is preferably from 7 to 30% by mass and more preferably from 9 to 20% by mass. When the content of the polymer block (A) in the hydrogenated block copolymer (a) is less than 5% by mass, the tube obtained from the resulting resin composition tends to be deteriorated in mechanical strength. Whereas, when the content of the polymer block (A) in the hydrogenated block copolymer (a) is more than 40% by mass, the tube obtained from the resulting resin composition tends to be undesirably deteriorated in transparency.

It is also important that the content of the polymer block (C) in the hydrogenated block copolymer (b) lies within the range of from 10 to 40% by mass on the basis of a total amount of the hydrogenated block copolymer (b). The content of the polymer block (C) is preferably from 15 to 35% by mass and more preferably from 20 to 35% by mass. When the content of the polymer block (C) in the hydrogenated block copolymer (b) is less than 10% by mass, the tube obtained from the resulting resin composition tends to be deteriorated in mechanical strength. Whereas, when the content of the polymer block (C) in the hydrogenated block copolymer (b) is more than 40% by mass, the tube obtained from the resulting resin composition tends to be undesirably deteriorated in transparency.

The hydrogenation rate of the polymer block (B) in the hydrogenated block copolymer (a), namely the hydrogenation rate of a carbon-to-carbon double bond derived from the butadiene unit contained in the polymer block (B) or the hydrogenation rate of a carbon-to-carbon double bond derived from the mixed unit of an isoprene unit and a butadiene unit contained in the polymer block (B), is 70% or more, preferably 80% or more and still more preferably from 85 to 95%. When the hydrogenation rate of the polymer block (B) in the hydrogenated block copolymer (a) is less than 70%, the tube obtained from the resulting resin composition tends to be deteriorated in transparency. Meanwhile, the "hydrogenation rate" as used herein means a rate of addition of hydrogen to the block copolymer which is determined by measuring iodine values of the block copolymer before and after subjected to the hydrogenation reaction.

The hydrogenation rate of the polymer block (D) in the hydrogenated block copolymer (b), namely the hydrogenation rate of a carbon-to-carbon double bond derived from the butadiene unit contained in the polymer block (D) or the hydrogenation rate of a carbon-to-carbon double bond derived from the mixed unit of an isoprene unit and a butadiene unit contained in the polymer block (D), is 80% or more, preferably 90% or more and still more preferably 95% or more. When the hydrogenation rate of the polymer block (D) in the hydrogenated block copolymer (b) is less than 80%, the tube obtained from the resulting resin composition tends to be deteriorated in transparency.

The hydrogenated block copolymer (a) used in the present invention has a glass transition temperature of from −45 to 30° C., preferably from −40 to 10° C. and more preferably from −40 to 0° C. When the glass transition temperature of the hydrogenated block copolymer (a) is lower than −45° C., the tube obtained from the resulting resin composition tends to be deteriorated in transparency, whereas when the glass transition temperature of the hydrogenated block copolymer (a) is higher than 30° C., the tube obtained from the resulting resin composition tends to be undesirably deteriorated in low-temperature impact resistance. Meanwhile, the "glass transition temperature" as used herein means a glass transition temperature as measured at a temperature rise rate of 10° C./min using a differential scanning calorimeter.

Also, the hydrogenated block copolymer (b) used in the present invention has a glass transition temperature of less than −45° C., preferably from −65 to −50° C. and more preferably from −60 to −50° C. When the glass transition temperature of the hydrogenated block copolymer (b) is −45° C. or higher, the tube obtained from the resulting resin composition tends to be deteriorated in anti-kinking property and anti-sticking property.

The hydrogenated block copolymer (a) used in the present invention contains at least one polymer block (A) and at least one polymer block (B), and the hydrogenated block copolymer (b) used in the present invention contains at least one polymer block (C) and at least one polymer block (D). The bonding type between the polymer blocks (A) and (B) in the hydrogenated block copolymer (a) and the bonding type between the polymer blocks (C) and (D) in the hydrogenated block copolymer (b) may be respectively of either a linear type, a branched type, a radial type or a combination of any two or more thereof.

Examples of the hydrogenated block copolymer (a) and the hydrogenated block copolymer (b) include di-block copolymers represented by X-Y, tri-block copolymers represented by X-Y-X or Y-X-Y, tetra-block copolymers represented by X-Y-X-Y, penta-block copolymers represented by Y-X-Y-X-Y or X-Y-X-Y-X, (X-Y)$_n$Z type copolymers and a mixture thereof wherein X is the polymer block (A) or the polymer block (C); Y is the polymer block (B) or the polymer block (D); Z is a residue of a coupling agent; and n is an integer of 3 or more.

When the same kinds of polymer blocks are linearly bonded to each other through a divalent coupling agent, a whole structure of the polymer blocks linearly bonded together is regarded and dealt with herein as one polymer block. For this reason, the polymer block which is to be inherently expressed by X-Z-X in the strict sense is generally represented merely by X except for the case where the polymer block must be distinguished from the polymer blocks composed of X solely. According to the above definition of the polymer blocks containing the residue of coupling agent, the block copolymer containing the residue of coupling agent which is to be inherently expressed, for example, by X-Y-Z-Y-X in the strict sense may be represented by X-Y-X which is an example of the tri-block copolymers.

Among the above copolymers, the tri-block copolymers are desirably used. It is preferred that the hydrogenated block copolymer (a) of a A-B-A type be used in combination with the hydrogenated block copolymer (b) of a C-D-C type wherein A is the polymer block (A), B is the polymer block (B), C is the polymer block (C) and D is the polymer block (D). When using the tri-block copolymer in combination with the di-block copolymer as the hydrogenated block copolymer (b), a combination of the copolymer of a C-D-C type and the copolymer of a C-D type is preferably used.

The hydrogenated block copolymer (a) used in the present invention is preferably in the form of a hydrogenated tri-block copolymer formed by hydrogenating a block copolymer having a A1-B-A2 type structure which is composed of a polymer block (A1) and a polymer block (A2) each constituted mainly from an aromatic vinyl compound unit, and the polymer block (B) constituted mainly from a mixed unit of an isoprene unit and a 1,3-butadiene unit.

The weight-average molecular weight of the polymer block (A1) is preferably from 150 to 60,000 and more preferably from 300 to 40,000. The weight-average molecular weight of the polymer block (A2) is preferably from 750 to 120,000 and more preferably from 1,500 to 80,000. The ratio of the weight-average molecular weight [Mw(A1)] of the polymer block (A1) to the weight-average molecular weight [Mw(A2)] of the polymer block (A2) [Mw(A1)/Mw(A2)] is preferably in the range of from 0.10 to 1.00 from the viewpoints of a good fluidity of the resulting resin composition and good transparency and flexibility of tubes obtained from the resin composition. In particular, from the viewpoints of good transparency and flexibility of the tubes, the ratio [Mw(A1)/Mw(A2)] is more preferably from 0.20 to 0.60 and still more preferably from 0.25 to 0.50.

When the hydrogenated block copolymer (a) used in the present invention includes the above hydrogenated tri-block copolymer having a A1-B-A2 type structure in which the ratio [Mw(A1)/Mw(A2)] lies within the range of from 0.10 to 1.00, the hydrogenated tri-block copolymer may also be used in combination with a hydrogenated tri-block copolymer of a A3-B-A4 type which contains a polymer block (A3) and a polymer block (A4) each constituted mainly from an aromatic vinyl compound unit and the polymer block (B) constituted mainly from a 1,3-butadiene unit, and in which the ratio of a weight-average molecular weight [Mw(A3)] of the polymer block (A3) to a weight-average molecular weight [Mw(A4)] of the polymer block (A4) [Mw(A3)/Mw(A4)] lies within the range of from 0.10 to 1.00.

The weight-average molecular weight of the polymer block (A3) is preferably from 150 to 60,000 and more preferably from 300 to 40,000. The weight-average molecular weight of the polymer block (A4) is preferably from 750 to 120,000 and more preferably from 1,500 to 80,000.

Meanwhile, the "weight-average molecular weight" as used herein means a weight-average molecular weight in terms of polystyrene as measured by gel permeation chromatography (GPC).

The weight-average molecular weight of each of the hydrogenated block copolymers (a) and (b) used in the present invention is preferably from 30,000 to 300,000, more preferably from 50,000 to 250,000 and still more preferably from 60,000 to 200,000. When the weight-average molecular weight of each of the hydrogenated block copolymers (a) and (b) lies within the range of from 30,000 to 300,000, the resulting tube desirably exhibits a good mechanical strength.

As the respective hydrogenated block copolymers (a) and (b), those copolymers having the above-mentioned molecular structures may be used singly, or may be used in combination of any two or more thereof which are different in molecular structure from each other. From the viewpoint of a good transparency, the hydrogenated block copolymer (b) is combination of a tri-block copolymer and a di-block copolymer.

[Production of Hydrogenated Block Copolymers (a) and (b)]

The process for producing the respective hydrogenated block copolymers (a) and (b) used in the present invention is not particularly limited. For example, the hydrogenated block copolymers (a) and (b) may be respectively produced by an anionic polymerization method.

Specific examples of the polymerization method include:

(i) Method of sequentially polymerizing an aromatic vinyl compound, a conjugated diene and an aromatic vinyl compound in the presence of an alkyl lithium compound as a polymerization initiator;

(ii) method of sequentially polymerizing an aromatic vinyl compound and a conjugated diene in the presence of an alkyl lithium compound as a polymerization initiator and then adding a coupling agent to the resulting polymer to allow the polymer to undergo a coupling reaction;

(iii) method of sequentially polymerizing a conjugated diene and then an aromatic vinyl compound in the presence of a dilithium compound as a polymerization initiator; etc.

Examples of the alkyl lithium compound include methyl lithium, ethyl lithium, n-butyl lithium, sec-butyl lithium, tert-butyl lithium and pentyl lithium. Examples of the coupling agent include dichloromethane, dibromomethane, dichloroethane, dibromoethane, dibromobenzene and phenyl benzoate. Examples of the dilithium compound include naphthalene dilithium and dilithiohexyl benzene.

The amounts of the polymerization initiator such as the alkyl lithium compounds and the dilithium compounds and the coupling agent used in the present invention may be appropriately determined depending upon a desired weight-average-molecular weight of the respective hydrogenated block copolymers (a) and (b) as aimed. The polymerization initiator such as the alkyl lithium compounds and the dilithium compounds is usually used in an amount of from 0.01 to 0.2 part by mass on the basis of 100 parts by mass of a sum of the polymerizable monomers used in the polymerization reaction such as an aromatic vinyl compound, 1,3-butadiene and isoprene. When using the coupling agent, the polymerization initiator is used in an amount of from 0.001 to 0.8 part by mass on the basis of 100 parts by mass of a sum of the polymerizable monomers.

The anionic polymerization is preferably carried out in the presence of a solvent. The solvent is not particularly limited as long as it is inert to the polymerization initiator and unless it adversely affects the polymerization reaction. Examples of the solvent include saturated aliphatic hydrocarbons and aromatic hydrocarbons such as hexane, heptane, octane, decane, toluene, benzene and xylene. In the polymerization reaction which may be carried out by any of the above methods (i) to (iii), the reaction temperature is usually from 0 to 80° C. and preferably from 10 to 70° C., and the reaction time is usually from 0.5 to 50 h and preferably from 1 to 30 h.

In order to control a glass transition temperature of the hydrogenated block copolymer (a) to the range of from −45 to 30° C., it is desirable that by adding a Lewis base as a co-catalyst in an amount of from 0.5 to 10 parts by mass and preferably from 2 to 7 parts by mass per 100 parts by mass of the monomers used in the polymerization, the amount of the 1,3-butadiene unit bonded or the amounts of the isoprene unit and the 1,3-butadiene unit bonded in the polymer block (B) of the hydrogenated block copolymer (a), more specifically, the content of a 1,2-bond and a 3,4-bond therein, is preferably adjusted to 40% or more, more preferably 50% or more and still more preferably 55% or more.

When the glass transition temperature of the hydrogenated block copolymer (b) is controlled to less than −45° C., it is desirable that by adding no Lewis base, or by adding the Lewis base in an amount of less than 0.5 part by mass per 100 parts by mass of the monomers used in the polymerization, the amount of the 1,3-butadiene unit bonded or the amounts of the isoprene unit and the 1,3-butadiene unit bonded in the polymer block (D) of the hydrogenated block copolymer (b), more specifically, the content of a 1,2-bond and a 3,4-bond therein, is preferably adjusted to less than 40%, more preferably 35% or less and still more preferably 30% or less.

Examples of the Lewis base usable in the present invention include ethers such as dimethyl ether, diethyl ether and tetrahydrofuran; glycol ethers such as ethylene glycol dimethyl ether and diethylene glycol dimethyl ether; and amines such as triethyl amine, N,N,N',N'-tetramethylene diamine and N-methyl morpholine. These Lewis bases may be used singly or in combination of any two or more thereof.

The amount of the Lewis base added may be determined depending upon to what extent the amount of the 1,3-butadiene unit bonded or the amounts of the isoprene unit and the 1,3-butadiene unit bonded in the polymer block (B) and the polymer block (D) is to be controlled. For this reason, the amount of the Lewis base added is not particularly limited. However, the Lewis base is usually used in an amount of from 0.1 to 1,000 mol and preferably from 1 to 100 mol per 1 gram atom of lithium contained in the alkyl lithium compound or dilithium compound used as the polymerization initiator.

After completion of the polymerization carried out by the above method, the resulting polymerization reaction solution containing the block copolymer may be poured into a poor solvent for the block copolymer such as methanol to solidify the block copolymer, or the polymerization reaction solution may be poured together with a steam into hot water to remove the solvent by azeotropic method (steam stripping), followed by drying the resulting solids, to produce a non-hydrogenated block copolymer (a) and a non-hydrogenated block copolymer (b).

Successively, the thus obtained block copolymers are subjected to hydrogenation reaction to produce the hydrogenated block copolymer (a) and the hydrogenated block copolymer (b). The hydrogenation reaction may be carried out in the presence of a hydrogenation catalyst such as a Raney nickel, a heterogeneous catalyst formed by supporting a metal such as Pt, Pd, Ru, Ph and Ni on a carrier such as carbon, alumina and diatomaceous earth, a Ziegler catalyst composed of combination of a transition metal compound with an alkyl aluminum compound, an alkyl lithium compound, etc., and a metallocene-based catalyst, by dissolving the respective block copolymers in a solvent inert to the hydrogenation reaction and hydrogenation catalyst to allow the block copolymers to react with hydrogen.

The hydrogenation reaction is carried out under a hydrogen pressure of usually from 0.1 to 20 MPa and preferably from 0.5 to 15 MPa at a temperature of usually from 20 to 250° C. and preferably from 50 to 150° C. for a period of from 0.1 to 100 h and preferably from 1 to 50 h.

The reaction solution obtained in the above polymerization which contains the respective block copolymers may also be directly subjected to hydrogenation reaction without isolating the block copolymers therefrom. In such a method, the hydrogenation reaction solution may be poured into a poor solvent such as methanol to solidify the respective block copolymers, or the hydrogenation reaction solution may be poured together with a steam into hot water to remove the solvent therefrom by azeotropic method (steam stripping), followed by drying the resulting solids, to produce the hydrogenated block copolymer (a) and the hydrogenated block copolymer (b).

The thus obtained hydrogenated block copolymer (a) and hydrogenated block copolymer (b) are pelletized by the conventionally known methods to obtain pellets of the hydrogenated block copolymer (a) and the hydrogenated block copolymer (b).

The pelletization of the block copolymers may be conducted, for example, by the method of extruding the hydrogenated block copolymer (a) and/or the hydrogenated block copolymer (b) from a single-screw or twin-screw extruder to form strands thereof and then cutting the respective stands in water by a cutting blade disposed at a front face of a die; and the method of extruding the hydrogenated block copolymer (a) and/or the hydrogenated block copolymer (b) from a single-screw or twin-screw extruder to form strands thereof, subjecting the thus extruded strands to water-cooling or air-cooling, and then cutting the respective stands by a strand cutter.

[Polyolefin-Based Resin (c)]

Examples of the polyolefin-based resin (c) used as the third component in the present invention include a propylene homopolymer, an ethylene homopolymer, a block copolymer or a random copolymer of propylene and ethylene having an ethylene content of from 1 to 30% by weight and preferably from 5 to 28% by weight, a block copolymer or a random copolymer of propylene and/or ethylene with an α-olefin which has an ethylene content of from 1 to 30% by weight and preferably from 5 to 28% by weight, an olefin-based thermoplastic elastomer, and a mixture thereof.

The propylene homopolymer may be, for example, a low-crystalline propylene homopolymer whose crystals have a heat of fusion (ΔH) of 100 J/g or less.

The olefin-based thermoplastic elastomer may be in the form of a copolymer constituted of (i) from 10 to 90% by weight of a hard segment such as a propylene homopolymer block or a copolymer block composed of 50% or more of a constitutional unit derived from propylene and less than 50% of a constitutional unit derived from ethylene, and (ii) from 90 to 10% by weight of a soft segment such as an ethylene homopolymer block, an ethylene-propylene rubber block and an ethylene-propylene-α-olefin copolymer block. Of these olefin-based thermoplastic elastomers, those produced by multi-stage polymerization are referred to as a reactor-type olefin-based thermoplastic elastomer.

Examples of the α-olefin in the above copolymer include those α-olefins having 20 or less carbon atoms such as 1-butene, 1-pentene, 3-methyl-1-butene, 1-hexene, 3-methyl-1-pentene, 4-methyl-1-pentene, 1-heptene, 1-octene, 1-nonene, 1-decene, 1-dodecene, 1-tetradecene, 1-hexadecene, 1-octadecene and 1-eicosene. These α-olefins may be used alone or in combination of any two or more thereof.

The content of the α-olefin copolymer unit in the above copolymer is usually from 1 to 30% by weight and preferably from 1 to 20% by weight on the basis of the weight of the copolymer.

Among the above polyolefin-based resins (c), preferred are a propylene homopolymer, a propylene-ethylene random copolymer having an ethylene content of from 1 to 30% by weight and preferably from 5 to 28% by weight, a propylene-1-butene random copolymer having a butene content of from 1 to 20% by weight, a propylene-ethylene-1-butene random copolymer having an ethylene content of from 1 to 25% by weight, a propylene-1-hexene random copolymer and a reactor-type olefin-based thermoplastic elastomer.

The melt flow rate (hereinafter occasionally referred to merely as "MFR") of the above polyolefin-based resin (c) as measured at 230° C. under a load of 21.2 N is preferably from 0.2 to 40 g/10 min, more preferably from 1 to 35 g/10 min, still more preferably from 2 to 30 g/10 min, further still more preferably from 3 to 28 g/10 min, further still more preferably from 5 to 30 g/10 min and most preferably from 20 to 30 g/10 min in view of a good anti-sticking property and a good clamp resistance of the resulting tube. When the polyolefin-based resin (c) is in the form of a propylene homopolymer, a copolymer of propylene and ethylene, or a mixture of thereof, the ethylene content therein is preferably from 0 to 30% by weight, more preferably from 5 to 28% by weight, still more preferably from 7 to 25% by weight and further still more preferably from 15 to 25% by weight from the viewpoint of a good flexibility.

Meanwhile, the ethylene content as used herein means the value calculated from IR spectrum of a press-molded article of a polymer which is measured according to the method described on page 616 of "New Edition-Handbook for Polymer Analysis" published by Kinokuniya Company Ltd. and edited by Association for Polymer Analysis, The Japan Society for Analytical Chemistry, 1995.

[Resin Composition Containing Components (a) to (c)]

The resin composition used in the present invention is composed of the hydrogenated block copolymer (a), the hydrogenated block copolymer (b) and the polyolefin-based resin (c).

When the hydrogenated block copolymer (a), the hydrogenated block copolymer (b) and the polyolefin-based resin (c) are compounded to prepare the resin composition, it is required that the mass ratio of the hydrogenated block copolymer (a) to the hydrogenated block copolymer (b) [(a)/(b)] is in the range of from 50/50 to 95/5. The mass ratio [(a)/(b)] is preferably from 55/45 to 80/20 and more preferably from 60/40 to 75/25. When the mass ratio of the hydrogenated block copolymer (a) in the above formulation of the hydrogenated block copolymers (a) and (b) is less than 50% by mass, the tube obtained from the resulting resin composition tends to be insufficient in transparency and flexibility. On the other hand, when the mass ratio of the hydrogenated block copolymer (a) is more than 95% by mass, the tube obtained from the resulting resin composition tends to be insufficient in anti-kinking property and anti-sticking property.

In the present invention, it is required not only that the mass ratio [(a)/(b)] satisfies the above-specified range, but also that the mass ratio of the polyolefin-based resin (c) to a sum of the hydrogenated block copolymer (a), the hydrogenated block copolymer (b) and the polyolefin-based resin (c) [(c)/((a)+(b)+(c))] lies within the range of from 10/100 to 60/100. The mass ratio [(c)/((a)+(b)+(c))] is preferably from 20/100 to 55/100 and more preferably from 30/100 to 50/100. When the mass ratio of the polyolefin-based resin (c) to a sum of the components (a), (b) and (c) is less than 10% by mass, the tube obtained from the resulting resin composition tends to be insufficient in anti-sticking property. On the other hand, when the mass ratio of the polyolefin-based resin (c) to a sum of the components (a), (b) and (c) is more than 60% by mass, the tube obtained from the resulting resin composition tends to be insufficient in solvent-bonding property.

The resin composition used in the present invention may contain other polymers unless inclusion of the polymers adversely affects the aimed objects of the present invention. Examples of the other polymers which may be contained in the resin composition include polyisoprene, polybutadiene, styrene-butadiene rubbers, styrene-isoprene rubbers, polyethylene, ethylene-vinyl acetate copolymers, ethylene-ethyl acrylate copolymers, ethylene-(meth)acrylic acid copolymers, metal ion-crosslinked resins (ionomers) of ethylene-(meth)acrylic acid copolymers, styrene-based resins such as polystyrene, AS resins and ABS resins, polyphenylene ether-based resins, polyamide-based resins such as nylon 6 and nylon 66, polyester-based resins such as polyethylene terephthalate and polybutylene terephthalate, polyurethane-based resins, acetal-based resins such as polyoxymethylene homopolymers and polyoxymethylene copolymers, and acrylic resins such as polymethyl(meth)acrylate-based resins.

However, from the viewpoint of effectively preventing sticking between the tubes, it is preferred that the resin composition contain no softening agent for rubbers.

The resin composition may also contain tackifier resins and inorganic fillers unless inclusion thereof adversely affects the aimed objects of the present invention.

Examples of the tackifier resins include rosin-based resins, terpene phenol resins, terpene resins, aromatic hydrocarbon-modified terpene resins, aliphatic petroleum resins, alicyclic petroleum reins, aromatic petroleum resins, coumarone-indene resins, phenol-based resins and xylene resins. The amount of the tackifier reins, if compounded, is preferably 50 parts by mass or less and more preferably 30 parts by mass or less per 100 parts by mass of a sum of the hydrogenated block copolymer (a), the hydrogenated block copolymer (b) and the polyolefin-based resin (c) from the viewpoint of a good anti-kinking property and a good anti-sticking property of the tube obtained from the resulting resin composition.

Examples of the inorganic fillers include talc, clay, mica, calcium silicate, calcium carbonate, magnesium carbonate, aluminum hydroxide, magnesium hydroxide, calcium hydroxide, silica, alumina, titanium oxide, iron oxide, zinc oxide and magnesium oxide. Although the resin composition of the present invention desirably contains no inorganic fillers in view of transparency, if any inorganic fillers are to be added to improve desired properties of the resin composition, the amount of the inorganic fillers added is preferably 3 parts by mass or less and more preferably 2 parts by mass or less per 100 parts by mass of a sum of the hydrogenated block copolymer (a), the hydrogenated block copolymer (b) and the polyolefin-based resin (c) from the viewpoint of a good transparency of the tube obtained from the resulting resin composition.

In addition, the resin composition of the present invention may also contain various other additives unless inclusion thereof adversely affects the aimed objects of the present invention. Examples of the additives include a processing heat stabilizer, a light stabilizer, an ultraviolet absorber, an antioxidant, a lubricant, a colorant, an anti-static agent, a flame retardant, a repellent, a water-proofing agent, a hydrophilic agent, a conductive agent, a thermal conductivity-imparting agent, an electromagnetic shielding agent, a transparency-controlling agent, a fluorescent agent, a slidability-imparting agent, a transparent agent, an anti-blocking agent, a metal deactivator and an anti-fungus agent.

Specific examples of the processing heat stabilizer include phosphorus-based processing heat stabilizers, lactone-based processing heat stabilizers and hydroxyl-based processing heat stabilizers. Among these processing heat stabilizers, preferred are lactone-based processing heat stabilizers. The content of the processing heat stabilizer in the resin composition is preferably 3 parts by mass or less and more preferably 2 parts by mass or less per 100 parts by mass of a sum of the hydrogenated block copolymer (a), the hydrogenated block copolymer (b) and the polyolefin-based resin (c) from the viewpoint of a good transparency of the tube obtained from the resulting resin composition.

The resin composition of the present invention may be produced by mixing the hydrogenated block copolymer (a), the hydrogenated block copolymer (b) and the polyolefin-based resin (c) as well as other optional components using a mixer such as a Henschel mixer, a V-blender, a ribbon blender, a tumbler blender and a conical blender, or thereafter melt-kneading the resulting mixture using a single-screw or twin-screw extruder, a kneader, etc. The resulting resin composition is preferably pelletized to facilitate molding of a tube therefrom. The melt-kneading temperature may be appropriately determined, and is usually from 150 to 300° C. and preferably from 180 to 250° C.

[Tube]

The tube of the present invention is produced from the above resin composition and may be formed into a desired shape by the following method. The method of producing the tube of the present invention is not particularly limited. For example, the resin composition prepared above is charged into an extruder, melted therein and extruded through a die into a tubular shape, and then the thus extruded tubular product is water-cooled or air-cooled to obtain a tube as a molded article. The extruder used in the above method may be either a single-screw extruder or a multi-screw extruder. Also, a plurality of extruders may be used to subject the resin composition to multilayer extrusion and thereby produce a molded article in the form of a multi-layered tube. Further, the tube may be molded by directly extruding the resin composition from an extruder upon production of the resin composition.

The shape of the tube obtained by the above method is not particularly limited, and is usually a circular or elliptical shape in section, etc. The size of the tube is not particularly limited. For example, the outer diameter of the tube is preferably from 1 to 50 mm, more preferably from 2 to 30 mm and still more preferably from 3 to 20 mm, and the wall thickness of the tube is preferably from 0.3 to 30 mm, more preferably from 0.4 to 20 mm and still more preferably from 0.5 to 10 mm.

In addition, the tube of the present invention may be laminated with one or more layers of the other polymers to form a multi-layered tube unless the aimed objects of the present invention are adversely affected thereby. Examples of the other polymers include olefin-based polymers such as polypropylene, polyethylene, ethylene-propylene copolymer rubbers (EPM) and ethylene-propylene-conjugated diene copolymer rubbers (EPDM); polyester-based polymers such as polyester elastomers, polyethylene terephthalate and polybutylene terephthalate; polyamide-based resins such as polyamide 6, polyamide 6.6, polyamide 6.10, polyamide 11, polyamide 12 and polyamide 6.12; acrylic resins such as poly(methyl acrylate) and poly(methyl methacrylate); polyoxymethylene-based resins such as polyoxymethylene homopolymers and polyoxymethylene copolymers; styrene-based resins such as styrene homopolymers, acrylonitrile-styrene resins and acrylonitrile-butadiene-styrene resins; polycarbonate resins; styrene-based elastomers and hydrogenated products or modified products thereof such as styrene-butadiene copolymer rubbers and styrene-isoprene copolymer rubbers; natural rubbers; synthetic isoprene rubbers, liquid polyisoprene rubbers and hydrogenated products or modified products thereof; chloroprene rubbers; acrylic rubbers; butyl rubbers; acrylonitrile-butadiene rubbers; epichlorohydrin rubbers; silicone rubbers; fluororubbers; chloro-sulfonated polyethylenes; urethane rubbers; polyurethane-based elastomers; polyamide-based elastomers; polyester-based elastomers; and soft vinyl chloride-based resins.

The above other polymers may be used alone or in combination of any two or more thereof to form a single layer or each of multiple laminated layers. When used in the laminated multiple layers, the kinds of polymers contained in the respective layers may be the same or different from each other.

The above polymer layer(s) of the tuber having a multi-layered structure may be used as either an innermost layer, an intermediate layer or an outermost layer according to desired properties to be imparted thereto. The multi-layered structure may be provided partially or intermittently in the tube, or portions of the multi-layered structure may be composed of different materials from each other.

In the present invention, in order to improve a pressure resistance, etc., while suppressing increase in wall thickness of the tube and maintaining a good flexibility thereof, a braided reinforcing yarn or a helical reinforcing member may be wound around the tube to form a pressure tube (hose). The braided reinforcing yarn may be provided inside or between the layers in the thickness direction of the tube. As the material of the braided reinforcing yarn, there may be used vinylon, polyamides, polyesters, aramid fibers, carbon fibers and metal wires. The helical reinforcing member may be wound over an outer peripheral surface of the tube. As the material of the helical reinforcing member, there may be used metals, plastics, etc.

[Medical Device]

In the medical device of the present invention, the above tube is used. Examples of the medical device include catheters used for infusion, blood transfusion, peritoneal dialysis, catheter intervention, etc., (such as intravascular catheters and balloon catheters), blood bags, synthetic vascular prostheses, vascular circuits, syringes, hemodialysers, blood cell separators, extracorporeal membrane oxygenation, dressing materials, and medical devices which are brought into contact with body fluids, in particular, blood.

Meanwhile, it is not required that whole portions of these medical devices are formed from the above resin composition, and at least portions of the medical devices which are brought into contact with body fluids may be formed therefrom. For example, in catheters or blood bags, the portions thereof which are brought into contact with body fluids may be formed from the resin composition, whereas the portions thereof which are not brought into contact with body fluids may be formed from other resins used for medical purposes such as soft vinyl chloride-based resins and polyurethanes.

EXAMPLES

The present invention will be described in more detail by reference to the following Examples. However, the Examples are only illustrative, and not intended to limit the invention thereto. In the following Reference Examples and Examples, various characteristic values were respectively measured by the following methods.

(1) Glass Transition Temperature of Hydrogenated Block Copolymer

Using a differential scanning calorimeter "DSC200" available from Seiko Instruments Inc., the hydrogenated block copolymer was heated at a temperature rise rate of 10° C./min to prepare a characteristic curve. The temperature at which an inflection point was observed was read out from the characteristic curve and determined as a glass transition temperature of the hydrogenated block copolymer.

(2) Content of Styrene in Block Copolymer and Contents of 1,2-Bond and 3,4-Bond Therein The measurement for 1H-NMR spectrum of the block copolymer was carried out, and the content of styrene in the block copolymer as well as the contents of 1,2-bond and 3,4-bond therein were calculated from the measurement results.

(3) Hydrogenation Rate of Block Copolymer

The iodine values of the block copolymer before and after subjected to hydrogenation reaction were measured, and the hydrogenation rate of the block copolymer was calculated from the ratio between the thus measured iodine values.

(4) Transparency

The respective resin compositions obtained in the following Examples and Comparative Examples were press-molded at 230° C. to prepare a test piece having a thickness of 1 mm (100 mm×100 mm×1 mm). The thus prepared test piece was measured for a haze value (%) as an index of its transparency using a haze meter "HR-100" available from Murakami Color Research Laboratory, according to ASTM D-1003. The smaller the haze value, the more excellent the transparency. The haze value of the resin composition is preferably 25% or less, more preferably 22% or less and still more preferably 20% or less.

(5) Flexibility

The respective resin compositions obtained in the following Examples and Comparative Examples were press-molded at 230° C. to prepare a test piece having a thickness of 1 mm (100 mm×100 mm×1 mm). The thus prepared test piece was measured for a hardness as an index of its flexibility using a type A hardness meter according to JIS K7215. The flexibility of the resin composition is preferably from 50 to 89, more preferably from 60 to 87 and still more preferably from 70 to 85.

(6) Anti-Kinking Property

The respective tubes each having a whole length of 20 cm (outer diameter: 40 mm; inner diameter: 30 mm; wall thickness: 0.5 mm) which were obtained in the following Examples and Comparative Examples were bent and deformed into a circular shape at 25° C. to measure a minimum bending diameter of the tube immediately before occurrence of kinking as an index of an anti-kinking property of the tube. The anti-kinking property of the tube is preferably 15 mm or less, more preferably 13 mm or less and still more preferably 10 mm or less.

(7) Anti-Sticking Property

The respective tubes each having a whole length of 1 m (outer diameter: 40 mm; inner diameter: 30 mm; wall thickness: 0.5 mm) which were obtained in the following Examples and Comparative Examples were formed into a loop having a diameter of 20 cm by double overhand knotting to allow knotted portions of the tube to stick together. The tube was pulled at its opposite ends at a pulling rate of 300 mm/min using a tensile tester to measure a stress value for initial several seconds as an index of an anti-sticking property thereof. Meanwhile, a kite string having a whole length of 1 m was inserted through the tube before being knotted so as to prevent elongation of the tube when subjected to the above tensile test. The anti-sticking property of the tube is preferably 20 N or less, more preferably 15 N or less and still more preferably 10 N or less.

(8) Fluidity

The respective resin compositions obtained in the following Examples and Comparative Examples were measured for MFR as an index of a fluidity thereof at 230° C. under a load of 2.16 kg according to JIS K7210. The fluidity of the resin composition is preferably 2 g/10 min or more, and more preferably 7 g/10 min or more.

(9) Clamp Resistance

An interior of the respective tubes each having a whole length of 200 mm (outer diameter: 40 mm; inner diameter: 30 mm; wall thickness: 0.5 mm) which were obtained in the following Examples and Comparative Examples was filled with a physiological salt solution and held upright, and then clamped at a height of 10 mm from the bottom with a forceps for medical tubes to prevent leakage of the physiological salt solution therefrom. After the elapse of 22 h, the forceps was released from the tube to allow the physiological salt solution in the tube to flow out from the bottom and measure the time required until the solution completely flowed out from the tube as an index of a clamp resistance thereof. The clamp resistance of the tube is preferably 9 s or shorter, more preferably 6 s or shorter and still more preferably 3 s or shorter.

(10) Solvent-Bonding Property

One end portion of the respective tubes each having a whole length of 70 mm (outer diameter: 40 mm; inner diameter: 30 mm; wall thickness: 0.5 mm) which were obtained in the following Examples and Comparative Examples was immersed by about 10 mm in cyclohexane. Then, a tubular portion (diameter: 40 mm) of a polypropylene connector was inserted by 5 mm into the end portion of the tube and bonded thereto. After the elapse of 24 h, the tube and the connector were pulled apart from each other to measure a tensile strength required for separation therebetween as an index of a solvent-bonding property of the tube. The solvent-bonding property of the tube is preferably 100 N or more, more preferably 110 N or more and still more preferably 120 N or more.

(11) Low-Temperature Impact Resistance

The respective resin compositions obtained in the following Examples and Comparative Examples were press-molded at 230° C. to prepare a 3 mm-thick test piece (10 mm×64 mm×3 mm; notched piece) according to JIS K-7110. The thus obtained test piece was cooled to −40° C. and then subjected to impact test using an Izod tester available from Toyo Seiki Co., Ltd., to measure an angle (°) of rise of a hammer at break of the test piece. An Izod impact strength of the tube was calculated from the thus measured angle of rise of a hammer and used as an index of a low-temperature impact resistance of the resin composition.

(12) Heat Resistance

The respective resin compositions obtained in the following Examples and Comparative Examples were press-molded at 230° C. to prepare two test pieces each having a thickness of 0.5 mm (25 mm×100 mm×0.5 mm). The two test pieces were bonded together, sandwiched between plates and then fixed with clips. The thus obtained test sample was subjected to sterilization in an autoclave (at 121° C. for 30 min). After the sterilization treatment, the test pieces were pulled apart from each other at a pulling rate of 30 cm/min using a tensile tester to measure a maximum stress value required for separation therebetween as an index of a heat resistance of the resin composition. The heat resistance of the resin composition is preferably 20 N or less, more preferably 15 N or less and still more preferably 10 N or less.

Reference Example 1

A pressure container previously purged with nitrogen and dried was charged with 80 L of cyclohexane as a solvent, 0.12 L of sec-butyl lithium as an initiator and 0.3 L of tetrahydrofuran as a Lewis base, and the contents of the pressure container were heated to 50° C., mixed with 0.39 L of styrene and then polymerized for 3 h. Successively, the thus obtained reaction solution was mixed with a mixed solution of 6.8 L of isoprene and 7.5 L of butadiene and polymerized for 4 h, and then mixed with 1.18 L of styrene and polymerized for 3 h. The resulting polymerization reaction solution was poured into 80 L of methanol to precipitate solids, and the precipitated solids were removed by filtration therefrom and then dried at 50° C. for 20 h, thereby obtaining a polystyrene-polyisoprene/polybutadiene-polystyrene tri-block copolymer having a content of 1,2-bond and 3,4-bond of 65%. Then, 10 kg of the thus obtained polystyrene-polyisoprene/polybutadiene-polystyrene tri-block copolymer were dissolved in 200 L of cyclohexane, and the resulting solution was mixed with palladium carbon as a hydrogenation catalyst (amount of palladium supported: 5% by mass) in an amount of 5% by mass on the basis of the copolymer and reacted at a hydrogen pressure of 2 MPa and a temperature of 150° C. for 10 h. The resulting reaction mixture was allowed to stand for cooling and release of pressure, and then palladium carbon was removed by filtration therefrom to obtain a filtrate. The thus obtained filtrate was concentrated and further vacuum-dried, thereby producing a hydrogenated polystyrene-polyisoprene/polybutadiene-polystyrene tri-block copolymer (hereinafter referred to merely as a "hydrogenated copolymer (1)"). As a result, it was confirmed that the thus obtained hydrogenated copolymer (1) had a ratio [Mw(A1)/Mw(A2)] of 0.30, a glass transition temperature of −30° C., a styrene content of 13% by mass, a hydrogenation rate of 85% and a weight-average molecular weight of 130,000.

Reference Example 2

The polymerization reaction and the hydrogenation reaction were carried out in the same manner as in Reference Example 1 except that 0.12 L of sec-butyl lithium as an initiator and 0.3 L of tetrahydrofuran as a Lewis base were charged, and 0.75 L of styrene, a mixed solution containing 6.0 L of isoprene and 7.0 L of butadiene, and 0.75 L of styrene, as monomers to be polymerized, were successively added and polymerized, thereby producing 9 kg of a hydrogenated polystyrene-polyisoprene/polybutadiene-polystyrene tri-block copolymer having a content of 1,2-bond and 3,4-bond of 65% (hereinafter referred to merely as a "hydrogenated copolymer (2)"). As a result, it was confirmed that the thus obtained hydrogenated copolymer (2) had a ratio [Mw(A1)/Mw(A2)] of 1.00, a glass transition temperature of −30° C., a styrene content of 14% by mass, a hydrogenation rate of 86% and a weight-average molecular weight of 130,000.

Reference Example 3

The polymerization reaction and the hydrogenation reaction were carried out in the same manner as in Reference Example 1 except that 0.18 L of sec-butyl lithium as an initiator and 0.1 L of N,N,N',N'-tetramethylene diamine as a Lewis base were charged, and 2.05 L of styrene, 16.6 L of butadiene and 4.1 L of styrene as monomers to be polymerized were successively added and polymerized, thereby producing 16 kg of a hydrogenated polystyrene-polybutadiene-polystyrene tri-block copolymer having a content of 1,2-bond of 80% (hereinafter referred to merely as a "hydrogenated copolymer (3)"). As a result, it was confirmed that the thus obtained hydrogenated copolymer (3) had a ratio [Mw(A1)/Mw(A2)] of 0.50, a glass transition temperature of −40° C., a styrene content of 35% by mass, a hydrogenation rate of 94% and a weight-average molecular weight of 100,000.

Reference Example 4

The polymerization reaction and the hydrogenation reaction were carried out in the same manner as in Reference Example 1 except that 0.18 L of sec-butyl lithium as an initiator as well as 2.20 L of styrene, a mixed solution containing 6.6 L of isoprene and 7.5 L of butadiene, and 2.20 L of styrene, as monomers to be polymerized, were successively added and polymerized, thereby producing 13 kg of a hydrogenated polystyrene-polyisoprene/polybutadiene-polystyrene tri-block copolymer having a content of 1,2-bond and 3,4-bond of 5% (hereinafter referred to merely as a "hydrogenated copolymer (4)"). As a result, it was confirmed that the thus obtained hydrogenated copolymer (4) had a ratio [Mw(A1)/Mw(A2)] of 1.00, a glass transition temperature of −55° C., a styrene content of 30% by mass, a hydrogenation rate of 98% and a weight-average molecular weight of 100,000.

Reference Example 5

The polymerization reaction and the hydrogenation reaction were carried out in the same manner as in Reference Example 1 except that 0.18 L of sec-butyl lithium as an initiator as well as 2.43 L of styrene, 16.6 L of butadiene and 2.43 L of styrene as monomers to be polymerized were successively added and polymerized, thereby producing 14 kg of a hydrogenated polystyrene-polybutadiene-polystyrene tri-block copolymer having a content of 1,2-bond of 5% (hereinafter referred to merely as a "hydrogenated copolymer (5)"). As a result, it was confirmed that the thus obtained hydrogenated copolymer (5) had a ratio [Mw(A1)/Mw(A2)] of 1.00, a glass transition temperature of −56° C., a styrene content of 30% by mass, a hydrogenation rate of 96% and a weight-average molecular weight of 100,000.

Reference Example 6

A pressure container previously purged with nitrogen and dried was charged with 80 L of cyclohexane as a solvent, 0.18 L of sec-butyl lithium as an initiator and 0.3 L of tetrahydrofuran as a Lewis base, and the contents of the pressure container were heated to 50° C., mixed with 2.0 L of styrene and then polymerized for 3 h. Successively, the thus obtained reaction solution was mixed with a mixed solution containing 19.0 L of butadiene and polymerized for 4 h. Thereafter, the resulting reaction solution was mixed with 30 g of a coupling agent (name of reagent: phenyl benzoate) and subjected to coupling reaction at 60° C. for 2 h. The resulting polymerization reaction solution was poured into 80 L of methanol to precipitate solids, and the precipitated solids were removed by filtration therefrom and then dried at 50° C. for 20 h, thereby obtaining a mixture containing 70% by mass of a polystyrene-polybutadiene-polystyrene tri-block copolymer having a content of 1,2-bond of 45% and 30% by mass of a polystyrene-polybutadiene di-block copolymer. Then, the thus obtained mixture of the tri-block and di-block copolymers was hydrogenated in the same manner as in Reference Example 1, thereby producing a mixture of a hydrogenated polystyrene-polybutadiene-polystyrene tri-block copolymer and a hydrogenated polystyrene-polybutadiene di-block copolymer (hereinafter referred to merely as a "hydrogenated copolymer (6)"). As a result, it was confirmed that the thus obtained hydrogenated copolymer (6) had a glass transition temperature of −58° C., a styrene content of 13% by mass, a hydrogenation rate of 98% and a weight-average molecular weight of 140,000.

Reference Example 7

The polymerization reaction and the hydrogenation reaction were carried out in the same manner as in Reference Example 1 except that 0.13 L of sec-butyl lithium as an initiator and 0.2 L of tetrahydrofuran as a Lewis base were charged, and 1.60 L of styrene, 16.0 L of isoprene and 1.60 L of styrene as monomers to be polymerized were successively added and polymerized, thereby producing 13 kg of a hydrogenated polystyrene-polyisoprene-polystyrene tri-block copolymer having a content of 1,2-bond and 3,4-bond of 75% (hereinafter referred to merely as a "hydrogenated copolymer (7)"). As a result, it was confirmed that the thus obtained hydrogenated copolymer (7) had a ratio [Mw(A1)/Mw(A2)] of 1.00, a glass transition temperature of −15° C., a styrene content of 21% by mass, a hydrogenation rate of 84% and a weight-average molecular weight of 120,000.

Reference Example 8

The polymerization reaction and the hydrogenation reaction were carried out in the same manner as in Reference Example 1 except that 0.17 L of sec-butyl lithium as an initiator as well as 1.40 L of styrene, 18.0 L of isoprene and 1.40 L of styrene as monomers to be polymerized were successively added and polymerized, thereby producing 14 kg of a hydrogenated polystyrene-polyisoprene-polystyrene tri-block copolymer having a content of 1,2-bond and 3,4-bond of 5% (hereinafter referred to merely as a "hydrogenated copolymer (8)"). As a result, it was confirmed that the thus obtained hydrogenated copolymer (8) had a ratio [Mw(A1)/Mw(A2)] of 1.00, a glass transition temperature of −58° C., a styrene content of 17% by mass, a hydrogenation rate of 95% and a weight-average molecular weight of 80,000.

Examples 1 to 23 and Comparative Examples 1 to 9

The respective hydrogenated block copolymers obtained in Reference Examples 1 to 8 were compounded with the following polyolefin-based resins (PP(1), PP(2), PP(3), PP(4), PE, PO(1) and PO(2)) at proportions shown in Tables 1 to 4. The resulting mixture was melt-kneaded at 230° C. using a twin-screw extruder and then pelletized to obtain pellets of a resin composition. The thus obtained pellets were evaluated for a fluidity thereof. Further, the pellets were press-molded to prepare a test piece which was then evaluated for a transparency, a flexibility, a low-temperature impact resistance and a heat resistance thereof by the above-mentioned methods. In addition, the pellets were molded at 230° C. using a single-screw extruder with a tube die, and the resulting molded product was rapidly cooled in a cooling vessel filled with water at 25° C. to obtain a tube having an inner diameter of 3 mm and an outer diameter of 4 mm. The thus obtained tube was evaluated for an anti-kinking property, an anti-sticking property, a clamp resistance and a solvent-bonding property thereof. The results are shown in Tables 1 to 4.

PP(1): Propylene-ethylene random copolymer [F327" (tradename) available from Prime Polymer Co., Ltd.; MFR: 7 g/10 min (230° C., 21.2 N); melting pint: 145° C.; ethylene content: 9%]

PP(2): Propylene-ethylene random copolymer ["F329RA" (tradename) available from Prime Polymer Co., Ltd.; MFR: 25 g/10 min (230° C., 21.2 N); melting pint: 135° C.; ethylene content: 22%]

PP(3): Propylene-ethylene random copolymer ["S331" (tradename) available from TPC Pte. Ltd.; MFR: 3 g/10 min (230° C., 21.2 N); melting pint: 134° C.; ethylene content: 7%]

PP(4): Propylene homopolymer ["S103L" (tradename) available from Prime Polymer Co., Ltd.; MFR: 4 g/10 min (230° C., 21.2 N); melting pint: 165° C.; ethylene content: 0%]

PE: Polyethylene homopolymer ["LF443" (tradename) available from Nippon Polyethylene Co., Ltd.; MFR: 2 g/10 min (230° C., 21.2 N); melting pint: 113° C.]

PO(1): Reactor-type olefin-based thermoplastic elastomer ["Zelas7053" (tradename) available from Mitsubishi Chemical Corp.; MFR: 7 g/10 min (230° C., 21.2 N); melting pint: 165° C.; ethylene content: 23%]

PO(2): Reactor-type olefin-based thermoplastic elastomer ["Zelas7023" (tradename) available from Mitsubishi Chemical Corp.; MFR: 2 g/10 min (230° C., 21.2 N); melting pint: 165° C.; ethylene content: 23%]

TABLE 1

|  | Examples | | | | | | |
| --- | --- | --- | --- | --- | --- | --- | --- |
|  | 1 | 2 | 3 | 4 | 5 | 6 | 7 |
| Hydrogenated block copolymer (a) | | | | | | | |
| Hydrogenated copolymer (1) | 40 | 35 | 0 | 40 | 0 | 0 | 40 |
| Hydrogenated copolymer (2) | 0 | 0 | 40 | 0 | 0 | 0 | 0 |
| Hydrogenated copolymer (3) | 0 | 0 | 0 | 0 | 40 | 40 | 0 |
| Hydrogenated block copolymer (b) | | | | | | | |
| Hydrogenated copolymer (4) | 20 | 25 | 20 | 0 | 20 | 0 | 20 |
| Hydrogenated copolymer (5) | 0 | 0 | 0 | 20 | 0 | 20 | 0 |

TABLE 1-continued

|  | Examples | | | | | | |
| --- | --- | --- | --- | --- | --- | --- | --- |
|  | 1 | 2 | 3 | 4 | 5 | 6 | 7 |
| Hydrogenated copolymer (6) | 0 | 0 | 0 | 0 | 0 | 0 | 0 |
| Hydrogenated copolymer (7) | 0 | 0 | 0 | 0 | 0 | 0 | 0 |
| Hydrogenated copolymer (8) | 0 | 0 | 0 | 0 | 0 | 0 | 0 |
| Polyolefin-based resin (c) | | | | | | | |
| PP(1) | 40 | 40 | 40 | 40 | 40 | 40 | 0 |
| PP(2) | 0 | 0 | 0 | 0 | 0 | 0 | 40 |
| PP(3) | 0 | 0 | 0 | 0 | 0 | 0 | 0 |
| PP(4) | 0 | 0 | 0 | 0 | 0 | 0 | 0 |
| PE | 0 | 0 | 0 | 0 | 0 | 0 | 0 |
| Properties | | | | | | | |
| Transparency (haze: %) | 19 | 20 | 23 | 21 | 25 | 23 | 18 |
| Flexibility (hardness: Type A) | 87 | 89 | 89 | 87 | 89 | 89 | 85 |
| Anti-kinking property (diameter: mm) | 13 | 11 | 14 | 13 | 14 | 15 | 13 |
| Anti-sticking property (N) | 12 | 15 | 18 | 17 | 20 | 20 | 5 |
| Fluidity (g/10 min) | 2.9 | 2.5 | 2 | 2.5 | 2.4 | 3 | 6.1 |
| Clamp resistance (time: s) | 5 | 4 | 8 | 8 | 9 | 9 | 1 |
| Solvent-bonding property (N) | 121 | 118 | 108 | 107 | 101 | 101 | 128 |
| Low-temperature impact resistance (kJ/m$^2$) | NB | NB | NB | NB | NB | NB | NB |
| Heat resistance (N) | 8 | 8 | 17 | 18 | 17 | 18 | 7 |

Note:
NB: The test piece was not broken.

TABLE 2

|  | Examples | | | | | | |
| --- | --- | --- | --- | --- | --- | --- | --- |
|  | 8 | 9 | 10 | 11 | 12 | 13 | 14 |
| Hydrogenated block copolymer (a) | | | | | | | |
| Hydrogenated copolymer (1) | 20 | 40 | 40 | 40 | 40 | 55 | 30 |
| Hydrogenated copolymer (2) | 0 | 0 | 0 | 0 | 0 | 0 | 0 |
| Hydrogenated copolymer (3) | 20 | 0 | 0 | 0 | 0 | 0 | 0 |
| Hydrogenated block copolymer (b) | | | | | | | |
| Hydrogenated copolymer (4) | 20 | 0 | 20 | 20 | 20 | 30 | 15 |
| Hydrogenated copolymer (5) | 0 | 0 | 0 | 0 | 0 | 0 | 0 |
| Hydrogenated copolymer (6) | 0 | 20 | 0 | 0 | 0 | 0 | 0 |
| Hydrogenated copolymer (7) | 0 | 0 | 0 | 0 | 0 | 0 | 0 |
| Hydrogenated copolymer (8) | 0 | 0 | 0 | 0 | 0 | 0 | 0 |
| Polyolefin-based resin (c) | | | | | | | |
| PP(1) | 40 | 0 | 0 | 0 | 0 | 0 | 0 |
| PP(2) | 0 | 40 | 0 | 0 | 0 | 15 | 55 |
| PP(3) | 0 | 0 | 40 | 0 | 0 | 0 | 0 |
| PP(4) | 0 | 0 | 0 | 40 | 0 | 0 | 0 |
| PE | 0 | 0 | 0 | 0 | 40 | 0 | 0 |
| Properties | | | | | | | |
| Transparency (haze: %) | 20 | 16 | 20 | 25 | 19 | 16 | 22 |
| Flexibility (hardness: Type A) | 88 | 84 | 88 | 89 | 70 | 65 | 89 |
| Anti-kinking property (diameter: mm) | 13 | 9 | 13 | 15 | 15 | 15 | 14 |
| Anti-sticking property (N) | 13 | 1 | 14 | 20 | 15 | 18 | 4 |
| Fluidity (g/10 min) | 2.8 | 8.5 | 1.6 | 3.2 | 1 | 2.8 | 8.1 |
| Clamp resistance (time: s) | 7 | 1 | 8 | 8 | 9 | 9 | 1 |
| Solvent-bonding property (N) | 106 | 128 | 115 | 105 | 110 | 130 | 127 |
| Low-temperature impact resistance (kJ/m$^2$) | NB | NB | NB | NB | NB | NB | NB |
| Heat resistance (N) | 17 | 7 | 10 | 5 | 20 | 9 | 5 |

Note:
NB: The test piece was not broken.

TABLE 3

|  | Examples | | | | | | | | |
|---|---|---|---|---|---|---|---|---|---|
|  | 15 | 16 | 17 | 18 | 19 | 20 | 21 | 22 | 23 |
| Hydrogenated block copolymer (a) | | | | | | | | | |
| Hydrogenated copolymer (1) | 35 | 50 | 55 | 0 | 0 | 35 | 55 | 40 | 40 |
| Hydrogenated copolymer (2) | 0 | 0 | 0 | 40 | 0 | 0 | 0 | 0 | 0 |
| Hydrogenated copolymer (3) | 0 | 0 | 0 | 0 | 40 | 0 | 0 | 0 | 0 |
| Hydrogenated block copolymer (b) | | | | | | | | | |
| Hydrogenated copolymer (4) | 25 | 10 | 5 | 20 | 20 | 0 | 0 | 0 | 0 |
| Hydrogenated copolymer (5) | 0 | 0 | 0 | 0 | 0 | 0 | 0 | 0 | 0 |
| Hydrogenated copolymer (6) | 0 | 0 | 0 | 0 | 0 | 25 | 5 | 20 | 20 |
| Hydrogenated copolymer (7) | 0 | 0 | 0 | 0 | 0 | 0 | 0 | 0 | 0 |
| Hydrogenated copolymer (8) | 0 | 0 | 0 | 0 | 0 | 0 | 0 | 0 | 0 |
| Polyolefin-based resin (c) | | | | | | | | | |
| PP(1) | 0 | 0 | 0 | 0 | 0 | 0 | 0 | 0 | 0 |
| PP(2) | 40 | 40 | 40 | 40 | 40 | 40 | 40 | 0 | 0 |
| PO(1) | 0 | 0 | 0 | 0 | 0 | 0 | 0 | 40 | 0 |
| PO(2) | 0 | 0 | 0 | 0 | 0 | 0 | 0 | 0 | 40 |
| PE | 0 | 0 | 0 | 0 | 0 | 0 | 0 | 0 | 0 |
| Properties | | | | | | | | | |
| Transparency (haze: %) | 18 | 17 | 17 | 22 | 24 | 16 | 15 | 17 | 17 |
| Flexibility (hardness: Type A) | 86 | 84 | 84 | 87 | 87 | 84 | 84 | 80 | 80 |
| Anti-kinking property (diameter: mm) | 13 | 12 | 12 | 14 | 14 | 9 | 9 | 13 | 15 |
| Anti-sticking property (N) | 5 | 17 | 18 | 11 | 13 | 1 | 2 | 13 | 17 |
| Fluidity (g/10 min) | 6 | 6.2 | 6.3 | 4.5 | 5 | 8.6 | 8 | 3.4 | 2.1 |
| Clamp resistance (time: s) | 1 | 9 | 9 | 4 | 5 | 1 | 1 | 5 | 7 |
| Solvent-bonding property (N) | 129 | 130 | 130 | 115 | 108 | 128 | 129 | 128 | 128 |
| Low-temperature impact resistance (kJ/m$^2$) | NB | NB | NB | NB | NB | NB | NB | NB | NB |
| Heat resistance (N) | 7 | 7 | 7 | 16 | 16 | 7 | 7 | 13 | 15 |

Note:
NB: The test piece was not broken.

TABLE 4

|  | Comparative Examples | | | | | | | | |
|---|---|---|---|---|---|---|---|---|---|
|  | 1 | 2 | 3 | 4 | 5 | 6 | 7 | 8 | 9 |
| Hydrogenated block copolymer (a) | | | | | | | | | |
| Hydrogenated copolymer (1) | 60 | 20 | 0 | 0 | 0 | 30 | 0 | 0 | 0 |
| Hydrogenated copolymer (2) | 0 | 0 | 0 | 0 | 0 | 0 | 0 | 0 | 0 |
| Hydrogenated copolymer (3) | 0 | 0 | 0 | 0 | 0 | 0 | 0 | 0 | 0 |
| Hydrogenated block copolymer (b) | | | | | | | | | |
| Hydrogenated copolymer (4) | 0 | 40 | 0 | 0 | 0 | 0 | 0 | 15 | 20 |
| Hydrogenated copolymer (5) | 0 | 0 | 20 | 20 | 0 | 0 | 30 | 0 | 0 |
| Hydrogenated copolymer (6) | 0 | 0 | 0 | 0 | 0 | 0 | 0 | 0 | 0 |
| Hydrogenated copolymer (7) | 0 | 0 | 0 | 40 | 40 | 0 | 30 | 30 | 40 |
| Hydrogenated copolymer (8) | 0 | 0 | 20 | 0 | 20 | 0 | 0 | 0 | 0 |
| Polyolefin-based resin (c) | | | | | | | | | |
| PP(1) | 40 | 40 | 40 | 40 | 40 | 70 | 40 | 55 | 0 |
| PP(2) | 0 | 0 | 0 | 0 | 0 | 0 | 0 | 0 | 40 |
| PP(3) | 0 | 0 | 0 | 0 | 0 | 0 | 0 | 0 | 0 |
| PP(4) | 0 | 0 | 0 | 0 | 0 | 0 | 0 | 0 | 0 |
| PE | 0 | 0 | 0 | 0 | 0 | 0 | 0 | 0 | 0 |
| Properties | | | | | | | | | |
| Transparency (haze: %) | 19 | 26 | 31 | 30 | 22 | 38 | 31 | 29 | 28 |
| Flexibility (hardness: Type A) | 85 | 91 | 90 | 89 | 89 | 95 | 92 | 90 | 88 |
| Anti-kinking property (diameter: mm) | 17 | 11 | 16 | 16 | 17 | 20 | 15 | 18 | 17 |
| Anti-sticking property (N) | 53 | 12 | 35 | 23 | 25 | 12 | 19 | 21 | 21 |

TABLE 4-continued

|  | Comparative Examples | | | | | | | | |
| --- | --- | --- | --- | --- | --- | --- | --- | --- | --- |
|  | 1 | 2 | 3 | 4 | 5 | 6 | 7 | 8 | 9 |
| Fluidity (g/10 min) | 3.7 | 1.6 | 4.6 | 2.8 | 3.7 | 5.4 | 4.1 | 2.4 | 7.5 |
| Clamp resistance (time: s) | 10 | 3 | 10 | 11 | 10 | 6 | 8 | 11 | 10 |
| Solvent-bonding property (N) | 82 | 106 | 92 | 102 | 103 | 62 | 89 | 85 | 90 |
| Low-temperature impact resistance (kJ/m$^2$) | 1.5 | NB | NB | NB | NB | 2.5 | NB | NB | NB |
| Heat resistance (N) | 24 | 7 | 21 | 22 | 23 | 14 | 21 | 21 | 23 |

Note:
NB: The test piece was not broken.

From the results shown in Tables 1 to 4, it was confirmed that the tubes obtained in Examples 1 to 23 which were produced from the resin compositions having an excellent fluidity were excellent in all of transparency, flexibility, anti-kinking property, anti-sticking property, clamp resistance, solvent-bonding property, low-temperature impact resistance and heat resistance.

On the contrary, the results of Comparative Examples 1 to 9 are as follows.

(1) It was confirmed that the tube obtained in Comparative Example 1 which contained no hydrogenated block copolymer (b) (corresponding to Example 1 of Patent Document 3) was deteriorated in anti-kinking property, anti-sticking property, clamp resistance, solvent-bonding property, low-temperature impact resistance and heat resistance.

(2) It was confirmed that the tube obtained in Comparative Example 2 was deteriorated in transparency, flexibility and fluidity owing to a small value of the mass ratio of the hydrogenated block copolymer (a) to the hydrogenated block copolymer (b) [(a)/(b)].

(3) It was confirmed that the tube obtained in Comparative Example 3 which contained no hydrogenated block copolymer (a) and contained the other hydrogenated block copolymer having a mid block composed of an isoprene unit solely was deteriorated in transparency, flexibility, anti-kinking property, anti-sticking property, clamp resistance, solvent-bonding property and heat resistance.

(4) It was confirmed that the tube obtained in Comparative Example 4 which contained no hydrogenated block copolymer (a) and contained the other hydrogenated block copolymers having a mid block composed of an isoprene unit solely was deteriorated in transparency, anti-kinking property, anti-sticking property, clamp resistance and heat resistance.

(5) It was confirmed that the tube obtained in Comparative Example 5 which contained no hydrogenated block copolymer (a) nor (b) and contained the other hydrogenated block copolymers each having a mid block composed of an isoprene unit solely was deteriorated in anti-kinking property, anti-sticking property, clamp resistance and heat resistance.

(6) It was confirmed that the tube obtained in Comparative Example 6 (corresponding to Example 2 of Patent Document 2) which contained no hydrogenated block copolymer (b) and has a large mass ratio of the component (c) to a sum of the components (a), (b) and (c) [(c)/((a)+(b)+(c))] was deteriorated in transparency, flexibility, anti-kinking property, solvent-bonding property and low-temperature impact resistance.

(7) It was confirmed that the tube obtained in Comparative Example 7 (corresponding to Invention Example 4 of Patent Document 5) which contained no hydrogenated block copolymer (a) and contained the other hydrogenated block copolymer having a mid block composed of an isoprene unit solely was deteriorated in transparency, flexibility, solvent-bonding property and heat resistance.

(8) It was confirmed that the tubes obtained in Comparative Examples 8 and 9 (corresponding to the formulations described in Example 1 of Patent Document 4 although no softening agent for rubbers was compounded therein) which contained no hydrogenated block copolymer (a) and contained the other hydrogenated block copolymer having a mid block composed of an isoprene unit solely were deteriorated in transparency, anti-kinking property, anti-sticking property, clamp resistance, solvent-bonding property and heat resistance.

INDUSTRIAL APPLICABILITY

As shown in the above Examples, the tube of the present invention is excellent in transparency, flexibility, anti-kinking property, anti-sticking property, clamp resistance, solvent-bonding property, low-temperature impact resistance and heat resistance. Owing to these excellent properties, the tube of the present invention can be suitably used in medical devices employed for infusion, blood transfusion, peritoneal dialysis, catheter intervention, etc. In addition to the medical applications, the tube of the present invention can be used as tubes for food transportation upon production of food and beverage, feeding of beverage in automatic vending machines, etc., tubes for domestic appliance parts for supply and discharge of water, etc., industrial tubes for car cleaning, etc., in various other applications requiring excellent flexibility and transparency.

What is claimed is:

1. A tube comprising a molded article of a resin composition, wherein the resin composition comprises:
    (a) a hydrogenated block copolymer having a glass transition temperature, $T_g(a)$, of from −45 to 30° C. and comprising, in reacted form, a polymer block (A) constituted mainly from an aromatic vinyl compound unit and a polymer block (B) constituted mainly from a 1,3-butadiene unit or constituted mainly from an isoprene unit and a 1,3-butadiene unit, wherein a content of the polymer block (A) is from 5 to 40% by mass based on a total mass of (a) and the polymer block (B) has a hydrogenation rate of 70% or more;
    (b) a hydrogenated block copolymer having a glass transition temperature, $T_g(b)$, of less than −45° C. and comprising, in reacted form, a polymer block (C) constituted mainly from an aromatic vinyl compound unit and a polymer block (D) constituted mainly from a 1,3-butadiene unit or constituted mainly from an isoprene unit and a 1,3-butadiene unit, wherein a content of the polymer block (C) is from 10 to 40% by mass based on a total mass of (b) and the polymer block (D) has a hydrogenation rate of 80% or more; and (c) a polyolefin-based resin having an ethylene content of from 22 to 30%, wherein the polyolefin-based resin (c) is selected from the group consisting of (i) a copolymer of propylene and ethylene and (ii) a mixture of a compolymer of propylene and ethylene and a propylene homopolymer, wherein a mass ratio of (a) to (b), (a)/(b), is from 50/50 to 95/5, and a mass ratio of (c) to a sum of (a), (b), and (c), (c)/((a)+(b)+(c)), is from 10/100 to 60/100.

2. The tube of claim 1, wherein the polymer block (B) is constituted mainly from an isoprene unit and a 1,3-butadiene unit.

3. The tube of claim 2, wherein the polymer block (D) is constituted mainly from an isoprene unit and a 1,3-butadiene unit.

4. The tube of claim 2, wherein the hydrogenated block copolymer (a) is a tri-block copolymer having a structure represented by:

A1-B-A2, wherein A1 is a first polymer block (A), A2 is a second polymer block (A), and B is the polymer block (B), wherein a mass ratio of a weight-average molecular weight, Mw(A1), of the polymer block (A1) to a weight-average molecular weight, Mw(A2), of the polymer block (A2), Mw(A1)/Mw(A2), is from 0.10 to 1.00.

5. The tube of claim 1, wherein the hydrogenated block copolymer (b) is a mixture of a tri-block copolymer and a di-block copolymer.

6. The tube of claim 1, wherein the polyolefin-based resin (c) is a polyolefin-based resin having a melt flow rate of from 0.2 to 50 g/10 min as measured at 230° C. under a load of 21.2 N.

7. A medical device, comprising the tube of claim 1.

8. The tube of claim 4, wherein the polymer block (D) is constituted mainly from an isoprene unit and a 1,3-butadiene unit.

9. The tube of claim 8, wherein the polyolefin-based resin (c) is a copolymer of propylene and ethylene.

10. The tube of claim 9, wherein the mass ratio, (c)/((a)+(b)+(c)), is from 20/100 to 55/100.

11. The tube of claim 9, wherein $T_g(a)$ is of from −40 to 10° C. and $T_g(b)$ is of from −65 to −50° C.

12. The tube of claim 9, wherein $T_g(a)$ is of from −40 to 0° C. and $T_g(b)$ is of from −60 to −50° C.

13. The tube of claim 9, wherein the mass ratio, Mw(A1)/Mw(A2), is from 0.25 to 0.5.

14. The tube of claim 4, wherein the polymer block (D) is constituted mainly from a 1,3-butadiene unit.

15. The tube of claim 14, wherein the hydrogenated block copolymer (b) is a mixture of a tri-block copolymer and a di-block copolymer.

16. The tube of claim 15, wherein the polyolefin-based resin (c) is a copolymer of propylene and ethylene.

17. The tube of claim 16, wherein the mass ratio, (c)/((a)+(b)+(c)), is from 20/100 to 55/100.

18. The tube of claim 16, wherein $T_g(a)$ is of from −40 to 10° C. and $T_g(b)$ is of from −65 to −50° C.

19. The tube of claim 16, wherein $T_g(a)$ is of from −40 to 0° C. and $T_g(b)$ is of from −60 to −50° C.

20. The tube of claim 16, wherein the mass ratio, Mw(A1)/Mw(A2), is from 0.25 to 0.5.

\* \* \* \* \*